(12) United States Patent
Stancer

(10) Patent No.: US 9,381,366 B2
(45) Date of Patent: Jul. 5, 2016

(54) METHODS AND APPARATUS FOR IMPROVED IPG RATE RESPONSE USING SUBCUTANEOUS ELECTRODES DIRECTLY COUPLED TO AN IMPLANTABLE MEDICAL DEVICE (IMD)

(75) Inventor: Christopher C. Stancer, Prescott, WI (US)

(73) Assignee: Medtronic, Inc., Minneapolis, MN (US)

( * ) Notice: Subject to any disclaimer, the term of this patent is extended or adjusted under 35 U.S.C. 154(b) by 2544 days.

(21) Appl. No.: 11/687,465

(22) Filed: Mar. 16, 2007

(65) Prior Publication Data

US 2008/0228234 A1    Sep. 18, 2008

(51) Int. Cl.
*A61N 1/365* (2006.01)
*A61N 1/375* (2006.01)
*A61B 5/042* (2006.01)
*A61N 1/05* (2006.01)

(52) U.S. Cl.
CPC .............. *A61N 1/375* (2013.01); *A61B 5/0422* (2013.01); *A61N 1/0504* (2013.01); *A61N 1/36585* (2013.01); *A61N 1/3756* (2013.01)

(58) Field of Classification Search
CPC ...................... A61N 1/36585; A61N 1/3756
USPC ..................................................... 607/9–28
See application file for complete search history.

(56) References Cited

U.S. PATENT DOCUMENTS

| | | |
|---|---|---|
| 3,983,867 A | 10/1976 | Case |
| 4,023,565 A | 5/1977 | Ohlsson |
| 4,082,086 A | 4/1978 | Page et al. |
| 4,121,576 A | 10/1978 | Greensite |
| 4,170,227 A | 10/1979 | Feldman et al. |
| 4,263,919 A | 4/1981 | Levin |
| 4,310,000 A | 1/1982 | Lindemans |
| 4,313,443 A | 2/1982 | Frosch et al. |
| 4,506,680 A | 3/1985 | Stokes |
| 4,593,702 A | 6/1986 | Kepski et al. |
| 4,817,606 A | 4/1989 | Lekholm |
| 4,907,593 A * | 3/1990 | Rapach et al. .................. 607/19 |
| 4,945,909 A * | 8/1990 | Fearnot et al. .................. 607/14 |
| 4,961,423 A | 10/1990 | Canducci |
| 5,331,966 A | 7/1994 | Bennett et al. |
| 5,513,644 A * | 5/1996 | McClure ............. A61N 1/3704 128/901 |
| 5,562,711 A * | 10/1996 | Yerich ............... A61N 1/36585 607/17 |
| 5,626,622 A * | 5/1997 | Cooper ............. A61N 1/36585 607/18 |
| 5,702,427 A * | 12/1997 | Ecker et al. ..................... 607/28 |
| 5,833,713 A | 11/1998 | Moberg |
| 5,899,927 A * | 5/1999 | Ecker et al. ..................... 607/23 |
| 6,208,900 B1 * | 3/2001 | Ecker et al. ..................... 607/17 |
| 6,804,555 B2 * | 10/2004 | Warkentin ........................ 607/9 |
| 6,871,096 B2 * | 3/2005 | Hill ................................ 607/25 |
| 6,885,891 B2 | 4/2005 | Cho et al. |

(Continued)

*Primary Examiner* — William Levicky
(74) *Attorney, Agent, or Firm* — Evans M. Mburu

(57) ABSTRACT

Per the disclosure subcutaneously implantable medical devices (IMDs) with rate responsive implantable pulse generator (IPG) capability that also include dual patient activity sensors are adaptively controlled. One of the activity sensors uses multiple electrodes adapted to acquire electrocardiographic signals and signals from non-cardiac muscle tissue (myopotentially-based signals). The signals from the electrode-based activity sensor are used to confirm and/or override the patient-activity sensor signals from the other non-myopotentially-based patient activity sensor. The electrodes are directly mechanically coupled to the housing of the IMD and electrically coupled to circuitry that filters, processes, and interprets both the patient activity sensor signals.

10 Claims, 7 Drawing Sheets

(56) References Cited

U.S. PATENT DOCUMENTS

| | | |
|---|---|---|
| 6,997,949 B2 | 2/2006 | Tuch |
| 7,181,284 B2* | 2/2007 | Burnes et al. .................. 607/25 |
| 2002/0128688 A1* | 9/2002 | Stoop et al. .................... 607/27 |
| 2003/0083700 A1* | 5/2003 | Hill ................................... 607/9 |
| 2005/0209648 A1* | 9/2005 | Burnes et al. .................... 607/9 |
| 2005/0209649 A1* | 9/2005 | Ferek-petric .................. 607/17 |
| 2005/0245988 A1* | 11/2005 | Miesel ................ A61B 5/0205 607/46 |
| 2006/0116730 A1* | 6/2006 | Gunderson .................... 607/17 |
| 2006/0136002 A1* | 6/2006 | Sheth et al. .................... 607/27 |
| 2006/0149328 A1* | 7/2006 | Parikh et al. .................... 607/28 |
| 2006/0155338 A1* | 7/2006 | Mongeon et al. ................. 607/9 |
| 2006/0217777 A1 | 9/2006 | Strom et al. |
| 2007/0191891 A1* | 8/2007 | Burnes et al. ..................... 607/9 |
| 2007/0191892 A1* | 8/2007 | Mullen et al. ..................... 607/9 |
| 2007/0255154 A1* | 11/2007 | Lu ........................ A61B 5/0006 600/520 |
| 2007/0255158 A1 | 11/2007 | Stancer et al. |

\* cited by examiner

METHODS AND APPARATUS FOR IMPROVED IPG RATE RESPONSE USING SUBCUTANEOUS ELECTRODES DIRECTLY COUPLED TO AN IMPLANTABLE MEDICAL DEVICE (IMD)

CROSS REFERENCE TO RELATED APPLICATIONS

The present patent document is related to co-pending non-provisional patent applications; namely, Ser. No. 11/085,843, entitled, "APPARATUS AND METHODS OF MONITORING CARDIAC ACTIVITY UTILIZING IMPLANTABLE SHROUD-BASED ELECTRODES," filed on 22 Mar. 2005 and Ser. No. 11/380,811 entitled, "SHROUD-BASED ELECTRODES HAVING VENTED GAPS," filed 28 Apr. 2006, the contents of which are hereby fully incorporated by reference herein.

FIELD OF THE INVENTION

The present invention relates generally to subcutaneously implantable medical devices (IMDs) that include a rate responsive implantable pulse generator (IPG) capability; and, more particularly to such devices having multiple electrodes adapted to acquire electrocardiographic signals and signals from non-cardiac muscle tissue. Subcutaneous IMDs according to the invention include both a primary patient-activity sensor (e.g., an accelerometer, a piezoelectric material, or the like) and electrodes adapted to detect myopotential signals that are used to confirm and/or override the patient-activity sensor signals. The electrodes are directly mechanically coupled to the housing of the IMD and electrically coupled to circuitry that filters and interprets the signals.

BACKGROUND OF THE INVENTION

The electrocardiogram (ECG) is commonly used in medicine to determine the status of the electrical conduction system of the human heart. As practiced the ECG recording device is commonly attached to the patient via ECG leads connected to pads arrayed on the patient's body so as to achieve a recording that displays the cardiac waveforms in any one of 12 possible vectors.

Since the implantation of the first cardiac IPG, implantable medical device technology has advanced with the development of sophisticated, programmable cardiac IPGs, IPG-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) that currently requires externally attached electrodes and the electrogram (EGM) that requires implanted pacing leads. The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. For example, S-T segment changes can be used to detect an ischemic episode. Acquisition and use of ECG tracing(s), on the other hand, has generally been limited to the use of an external ECG recording machine attached to the patient via surface electrodes of one sort or another.

The aforementioned ECG systems that utilize detection and analysis of the PQRST complex are all dependent upon the spatial orientation and number of electrodes available in or around the heart to pick up the depolarization wave front As the functional sophistication and complexity of implantable medical device systems increased over the years, it has become increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available which can even transmit a digitized electrical signal to display electrical cardiac activity (e.g., an ECG, EGM, or the like) for storage and/or analysis by an external device. The surface ECG, in fact, has remained the standard diagnostic tool since the very beginning of pacing and remains so today.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure used to determine cardiac status prior to implanting a pacing system; thereafter, the physician will normally use an ECG available through the programmer to check the IPG's efficacy after implantation. Such ECG tracings are placed into the patient's records and used for comparison to more recent tracings. It must be noted, however, that whenever an ECG recording is required (whether through a direct connection to an ECG recording device or to an IPG programmer), external electrodes and leads must be used.

Unfortunately, surface electrodes have some serious drawbacks. For example, electrocardiogram analysis performed using existing external or body surface ECG systems can be limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration or motion. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the IPG follow-up session. One possible approach is to equip the implanted IPG with the ability to detect cardiac signals and transform them into a tracing that is the same as or comparable to tracings obtainable via ECG leads attached to surface electrodes.

Previous art describes how to monitor electrical activity of the human heart for diagnostic and related medical purposes. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems, which combine surface EKG signals for artifact rejection.

The primary use for multiple electrode systems in the prior art is vector cardiography from ECG signals taken from multiple chest and limb electrodes. This is a technique whereby the direction of depolarization of the heart is monitored, as well as the amplitude. U.S. Pat. No. 4,121,576 issued to Greensite discusses such a system.

Numerous body surface ECG monitoring electrode systems have been employed in the past in detecting the ECG and conducting vector cardiographic studies. For example, U.S. Pat. No. 4,082,086 to Page, et al., discloses a four electrode orthogonal array that may be applied to the patient's skin both for convenience and to ensure the precise orientation of one electrode to the other. U.S. Pat. No. 3,983,867 to Case describes a vector cardiography system employing ECG electrodes disposed on the patient in normal locations and a hex axial reference system orthogonal display for displaying ECG signals of voltage versus time generated across sampled bipolar electrode pairs.

Another prior art approach includes U.S. Pat. No. 4,817,606 to Lekholm entitled, "Body Activity Controlled Heart Pacer" the contents of which are incorporated herein.

With regard to various aspects of time-release of surface coatings and the like for chronically implanted medical devices, the following issued patents are incorporated herein by reference. U.S. Pat. No. 6,997,949 issued 14 Feb. 2006 and entitled, "Medical device for delivering a therapeutic agent and method of preparation," and U.S. Pat. No. 4,506,680 entitled, "Drug dispensing body implantable lead." In the former patent, the following is described (from the Abstract section of the '949 patent) as follows: A device useful for localized delivery of a therapeutic agent is provided. The device includes a structure including a porous polymeric material and an elutable therapeutic agent in the form of a solid, gel, or neat liquid, which is dispersed in at least a portion of the porous polymeric material. Methods for making a medical device having blood-contacting surface electrodes is also provided.

Moreover, in regard to subcutaneously implanted EGM electrodes, the aforementioned Lindemans U.S. Pat. No. 4,310,000 discloses one or more reference sensing electrode positioned on the surface of the IPG case as described above. U.S. Pat. No. 4,313,443 issued to Lund describes a subcutaneously implanted electrode or electrodes for use in monitoring the ECG. Finally, U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

SUMMARY

The present invention provides a leadless subcutaneous (or submuscular) single or multiple-electrode array that provides various embodiments of a compliant surround shroud coupled to a peripheral portion of an implantable medical device (IMD). The shroud incorporates a plurality of substantially planar electrodes mechanically coupled within recessed portions of the shroud. These electrodes electrically couple to circuitry of an IMD and are adapted to detect cardiac activity of a subject. Temporal recordings of the detected cardiac activity are referred to herein as an extra-cardiac electrogram (EC-EGM). The recordings can be stored upon computer readable media within an IMD at various resolution (e.g., continuous beat-by-beat, periodic, triggered, mean value, average value, etc.). Real time or stored EC-EGM signals can be provided to remote equipment via telemetry. For example, when telemetry, or programming, head of an IMD programming apparatus is positioned within range of an IMD the programmer receives some or all of the EC-EGM signals.

The present invention relates generally to subcutaneously implantable medical devices (IMDs) and more particularly to such devices having multiple electrodes adapted to acquire electrocardiographic signals and signals from non-cardiac muscle tissue. Subcutaneous IMDs according to the invention include both a primary patient-activity sensor (e.g., an accelerometer, a piezoelectric material, or the like) and electrodes adapted to detect myopotential signals that are used to confirm and/or override the patient-activity sensor signals. The electrodes are directly mechanically coupled to the housing of the IMD and electrically coupled to circuitry that filters and interprets the signals.

Thus, according to the invention myopotential signals from non-cardiac muscle tissue indicate body motion, which while detrimental to sensing a clean cardiac signal, are used to confirm and/or override signals from a patient-activity sensor of the IMD. For example, the detected myopotential signals (due to body motion) are used in concert with a pre-existing activity sensor such as an accelerometer or piezoelectric sensor, to advance or retard a pacing rate in a physiologic manner. In one embodiment of the invention the myopotential signals are sensed for a predetermined amount of time before the pacing rate is advanced or retarded based at least in part upon said myopotential signals. Therefore, even if a patient was only moving their arms vigorously—which typically would not be detected or interpreted as exertion requiring advancement of a cardiac pacing rate by the patient-activity sensor—according to the invention the pacing rate would be increased, therefore avoiding a situation whereby a patient feels tired due to lack of cardiac output.

The present invention provides improved apparatus and methods for reliably collecting EC-EGM, patient activity and myopotential signals for use or collection in conjunction with diverse IMDs (e.g., implantable IPGs having endocardial leads, implantable cardioverter-defibrillators or ICDs, subcutaneous ICDs, submuscular ICDs, and the like).

Thus according to the invention a situation wherein a patient was in need of adequate perfusion due to essentially undetected exertion (e.g., sustained rapid arm movement) the detection of accompanying myopotential signals (muscle noise) can be used to adjust the pacing therapy rate. The situations wherein the invention thus has great utility would include weighlifting (wherein the patient's torso is substantially stationary), rowing a dinghy, swimming, deep water fishing, and the like. Furthermore, the situations can be defined as any activity wherein an accelerometer alone would not detect the sustained patient activity. Thus, the invention in general provides methods and apparatus to logically combine patient activity sensor signals from a pair of sensors (one of the pair of sensors being electrode-based and capable of sensing myopotential signals) to control a rate responsive cardiac pacing scheme.

The invention can be implemented employing suitable sensing amplifiers, switching circuits, signal processors, and memory to process the EC-EGM signals collected between any selected pair or pairs of the electrodes deployed in an array around the periphery or surface of a housing of an IMD to provide a leadless, orientation-insensitive means for receiving the EC-EGM signals from the heart. For example, circuitry such as described in prior art patent U.S. Pat. No. 5,833,713 to Moberg entitled, "Rate Responsive IPG Having an Accelerometer-based Physical Activity Sensor," the contents of which are hereby incorporated herein by reference. Per the '713 patent to Moberg, an accelerometer-based, multi-axis physical activity sensor for use with a rate-responsive IPG, and a method for fabricating the sensor, are provided. The multi-axis physical activity sensor includes a cantilever beam having a film of a piezoelectric polymer adhered to each surface of an electrically conductive substrate. The piezoelectric films are highly resistant to fracturing during manufacture and in use, and they provide a strong output signal when stressed in response to bodily accelerations. A mass is mounted to a free end of the cantilever beam, and is substantially offset with respect to a planar surface of the beam so as to impart multi-axis sensitivity to the physical activity sensor. The accelerometer-based, multi-axis physical activity sensor provides an output signal that is communicated to IPG circuitry using a pair of electrical conductors.

The instant patent disclosure also hereby incorporates by reference U.S. Pat. No. 6,885,891 to Cho et al. entitled, "Automatic Rate Response Sensor Mode Switch." According to certain aspects of the '891 patent an automatic rate response sensor mode switch is implemented in an IMD to monitor and isolate a sensor, such as an activity sensor, in an integrated sensor scheme. The isolated sensor is based on identification of problems associated with the sensor. The implantable medical device will switch to operate with the remainder sensor(s). Specifically, an algorithm tests and determines sensor status to initiate and operate the sensor mode switch. The software continuously monitors, isolates or qualifies a sensor to come back on-line automatically.

The shroud can comprise a non-conductive, bio-compatible material such as any appropriate resin-based material, urethane polymer, silicone, or relatively soft urethane that retains its mechanical integrity during manufacturing and prolonged exposure to body fluids. The shroud placed around the peripheral portions of an IMD can utilize a number of configurations (e.g., two, three, four recesses) for individual electrodes. However, a three-electrode embodiment appears to provide an improved signal-to-noise ratio. In one form of this embodiment the electrodes are located with approximately equal spacing therebetween (i.e., in an equilateral triangular configuration). And, embodiments having a single electrode pair appear much more sensitive (i.e., negatively) to appropriate orientation of the device relative to the heart than embodiments having more than a single pair of electrodes. Of course, embodiments of the invention using more than three electrodes increases complexity without providing a significant improvement in signal quality.

Embodiments having electrodes connected to three sense-amplifiers that are hardwired to three electrodes can record simultaneous EC-EGM signals. Alternative embodiments employ electrodes on the face of the lead connector, or header module, and/or major planar face(s) of the IPG that may be selectively or sequentially coupled in one or more pairs to the terminals of one or more sense amplifiers to pick up, amplify and process the EC-EGM signals across each electrode pair. In one aspect, the EC-EGM signals from a first electrode pair are stored and compared to other electrode pair(s) in order to determine the optimal sensing vector. Following such an optimization procedure, the system can be programmed to chronically employ the selected subcutaneous EC-EGM signal vector.

With respect to the elongated conductor coupling the planar electrodes to operative circuitry within an IMD, the assembly includes a unitary member stamped from a plate of conductive material such as titanium. In one embodiment the unitary member comprises a pre-shaped partially serpentine workpiece having a slightly curvilinear (i.e., substantially planar) major plate portion, a transition portion, and a partially serpentine portion adapted to cooperate with the configuration of the pre-configured conductor pathway.

For mass production of assemblies according to the invention a unique electrode piecepart can be fabricated for each unique conductor pathway and recess shape and configuration (including any of the variety of diverse mechanical interlocking features described hereinabove). Besides manufacturing processes such as metal stamping, the metallic electrode member(s) can be fabricating using electron discharge machining (EDM), laser cutting, or the like. It is desirable that the electrode assemblies are pre-configured (at least in a two-dimensional manner) so that little or no mechanical deformation or bending is required to fit each assembly into a shroud member. In addition, due to pre-configuring the parts the bends occur in a highly predictable manner and retain relatively little, if any, energy due to the spring-constant of the metal used to form the parts. In the event that electrical insulation or a dielectric layer becomes necessary or desirable, the major elongated portion of an electrode assembly can be coated with an insulative material such as paralyne or similar while the portions of the assembly likely to contact body fluid can be coating with diverse coatings pursuant to various embodiments of the invention.

Electrode assemblies according to the invention can be used for chronic or acute extra-cardiac electrogram (EC-EGM) signal sensing collection and attendant heart rate monitoring, capture detection, arrhythmia detection, and the like as well as detection of myriad other cardiac insults (e.g., ischemia monitoring using S-T segment changes, pulmonary edema monitoring based upon impedance changes).

In addition, the surface of the electrode can be treated with one or more electrode coatings to enhance signal-conducting, de- and re-polarization sensing properties, and to reduce polarization voltages (e.g., platinum black, titanium nitride, titanium oxide, iridium oxide, carbon, etc.). That is the surface area of the electrode surfaces may be increased by techniques known in the art. and/or can be coated with such materials as just described and equivalents thereof. All of these materials are known to increase the true electrical surface area to improve the efficiency of electrical performance by reducing wasteful electrode polarization, among other advantages.

Many of the embodiments of the inventive electrodes herein can provide a continuous electrical path free of welds or bonds on a portion of the planar electrode, the transition portion, the elongated conductor or the distal tip portion. Moreover, the electrode assembly according to the invention anchors to a shroud member free of any chemical or adhesive bonding materials that can cause excursions due to electroactive specie release to the electrode surface or portions thereof.

These and other advantageous aspects of the invention will be appreciated by those of skill in the art after studying the invention herein described, depicted and claimed. In addition, persons of skill in the art will appreciate insubstantial modifications of the invention that are intended to be expressly covered by the appended claims.

DETAILED DESCRIPTION OF THE DRAWINGS

Figure 1:
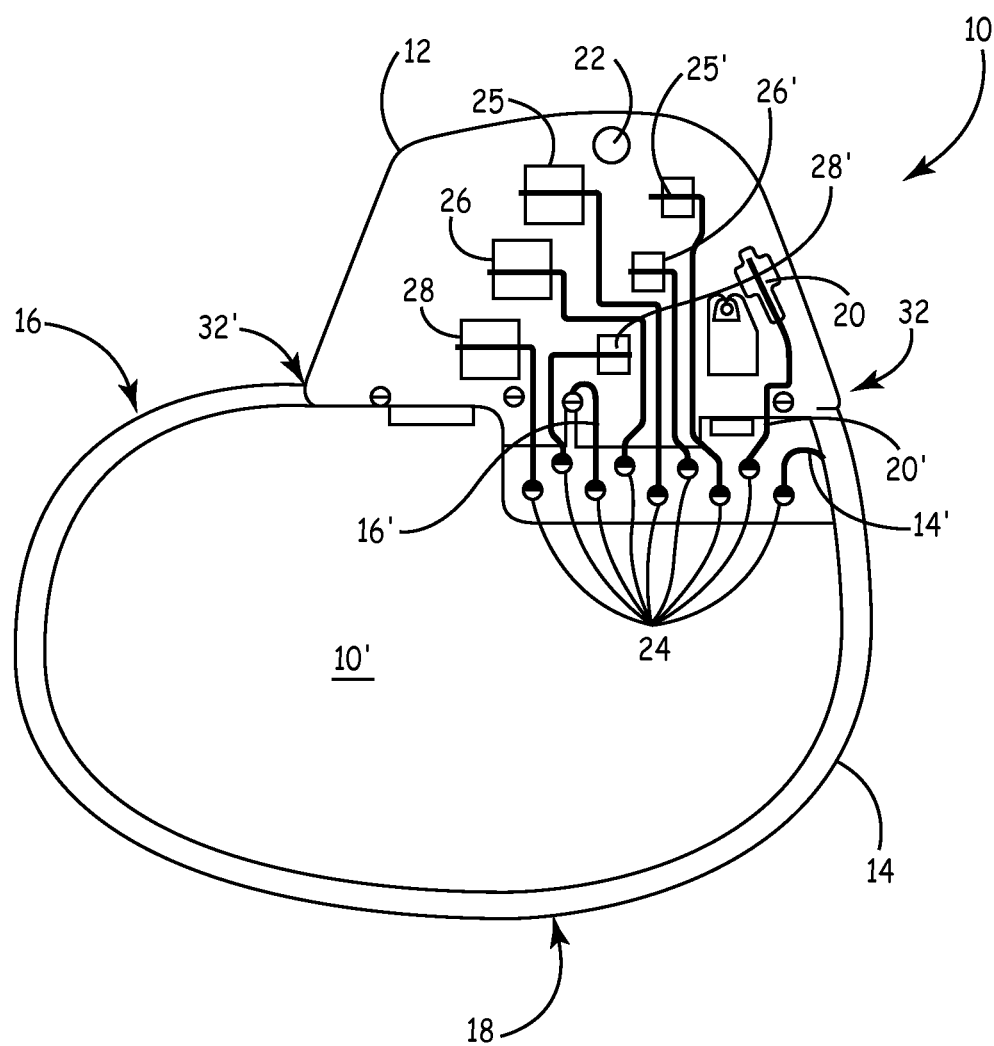
FIG. 1 is an elevational side view depicting an exemplary shroud assembly coupled to an IMD which illustrates electrical conductors disposed in the header, or connector, portion of the IMD which is configured to receive a proximal end portion of medical electrical leads (not shown).

FIG. 1 is an elevational side view depicting an exemplary shroud assembly 14 coupled to an IMD 10 which illustrates electrical conductors 24,25,26,28 disposed in the header, or connector, portion 12 of the IMD 10 which are configured to couple to end portions of medical electrical leads as well as couple to operative circuitry within the IMD housing (not shown). The shroud assembly 14 surrounds IMD 10 and mechanically couples to the header portion 12 and includes at least three discrete electrodes 16,18,20 adapted for sensing far-field, or extra-cardiac electrogram (EC-EGM) signals. FIG. 1 also depicts an aperture 22 formed within the header 12 which can be used to receive thread used to suture the header 12 (and thus the IMD 10) to a fixed surgical location (also known as a pocket) of a patient's body.

As partially depicted in FIG. 1, an elongated conductor 14' couples to electrode 14, elongated conductor 16' couples to electrode 16, and conductor segment 20' couples to electrode 20. Furthermore, three of the conductors (denoted collectively with reference numeral 24) couple to three cuff-type conductors 25,26,28 adapted to receive proximal portions of medical electrical leads while another three of the conductors couple to conductive pads 25',26',28' which are aligned with, but spaced from the conductors 25,26,28 along a trio of bores (denoted as 25",26",28" in FIG. 4 herein) formed in header 12.

Figure 2:
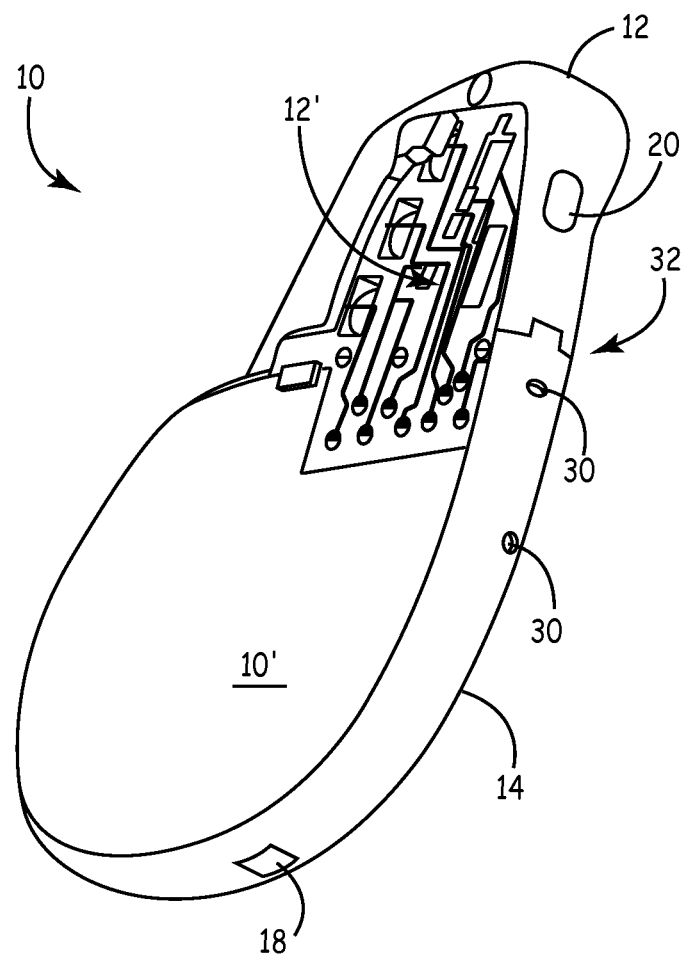
FIG. 2 is a perspective view of the IMD depicted in FIG. 1 further illustrating the shroud assembly.

FIG. 2 is a perspective view of the IMD 10 depicted in FIG. 1 further illustrating the shroud assembly 14 and two of the three electrodes 18,20. In addition, two of a plurality of adhesive ports 30 and a mechanical joint 32 between the elongated portion of the shroud assembly 14 and the header 12 are also depicted in FIG. 2. The ports 30 can be used to evacuate excess medical adhesive disposed between the shroud assembly 14 and the IMD 10 and/or used to inject medical adhesive into one or more ports 30 to fill the void(s) therebetween. In one form of the invention, a major lateral portion 12' of header 12 remains open to ambient conditions during assembly of the IMD 10. Subsequent to making electrical connections between the plurality of conductors of the shroud assembly 14 and the header 12, the open lateral portion 12' is sealed (e.g., automatically or manually filled with a biocompatible substance such as a substantially clear medical adhesive, such as Tecothane® made by Noveon, Inc. a wholly owned subsidiary of The Lubrizol Corporation). Thus most if not all of the plurality of conductors of the shroud assembly 14 and the IMD 10 are visible and can be manually and/or automatically inspected to ensure long term operability and highest quality of the completed IMD 10.

Some properties of various Tecothane® appear below (as published in the Technical Data Sheet (TDS) for certain clear grades of the material:

| Tecothane ® Typical Physical Test Data - CLEAR GRADES | | | | | | | | | |
|---|---|---|---|---|---|---|---|---|---|
| | ASTM Test | TT-1074A | TT-1085A | TT-1096A | TT-1056D | TT-1065D | TT-1069D | TT-1072D | TT-1076D-M |
| Durometer (Shore Hardness) | D2240 | 75A | 85A | 94A | 54D | 64D | 69D | 74D | 75D |
| Specific Gravity | D792 | 1.10 | 1.12 | 1.15 | 1.16 | 1.18 | 1.18 | 1.18 | 1.19 |
| Flexural Modulus (psi) | D780 | 1.300 | 3.000 | 8.000 | 19.000 | 26.000 | 44.000 | 73.000 | 180.000 |
| Ultimate Tensile (psi) | D412 | 6.000 | 7.000 | 9.000 | 9.600 | 10.000 | 8.800 | 9.000 | 8.300 |
| Ultimate Elongation (%) | D412 | 550 | 450 | 400 | 350 | 300 | 310 | 275 | 150 |
| Tensile (psi) | D412 | | | | | | | | |
| at 100% Elongation | | 500 | 800 | 1.300 | 2.500 | 2.800 | 3.200 | 3.700 | 3.600 |
| at 200% Elongation | | 700 | 1.000 | 2.100 | 3.800 | 4.600 | 4.200 | 3.900 | NA |
| at 300% Elongation | | 1.100 | 1.600 | 4.300 | 6.500 | 7.600 | NA | NA | NA |
| Melt Index (gm/10 min at 2160 gm lead) | D1238 | 3.5 (205° C.) | 4.0 (205° C.) | 3.8 (210° C.) | 4.0 (210° C.) | 2.0 (210° C.) | 3.0 (210° C.) | 2.0 (210° C.) | 5.0 (210° C.) |
| Mold Shrinkage (in/in) | D955 | .008-.012 | .008-.012 | .036-.019 | .004-.008 | .004-.008 | .004-.008 | .004-.006 | .004-.006 |

Referring again to FIG. 2, the terminal ends of conductors 24 are depicted to include the optional shaped-end portion which provides a target for reliable automatic and/or manual coupling (e.g., laser welding, soldering, and the like) of the terminal end portions to respective conductive pins of a multi-polar feedthrough assembly (not shown). As is known in the art, such conductive pins hermetically couple to operative circuitry disposed within the IMD 10.

Figure 3:
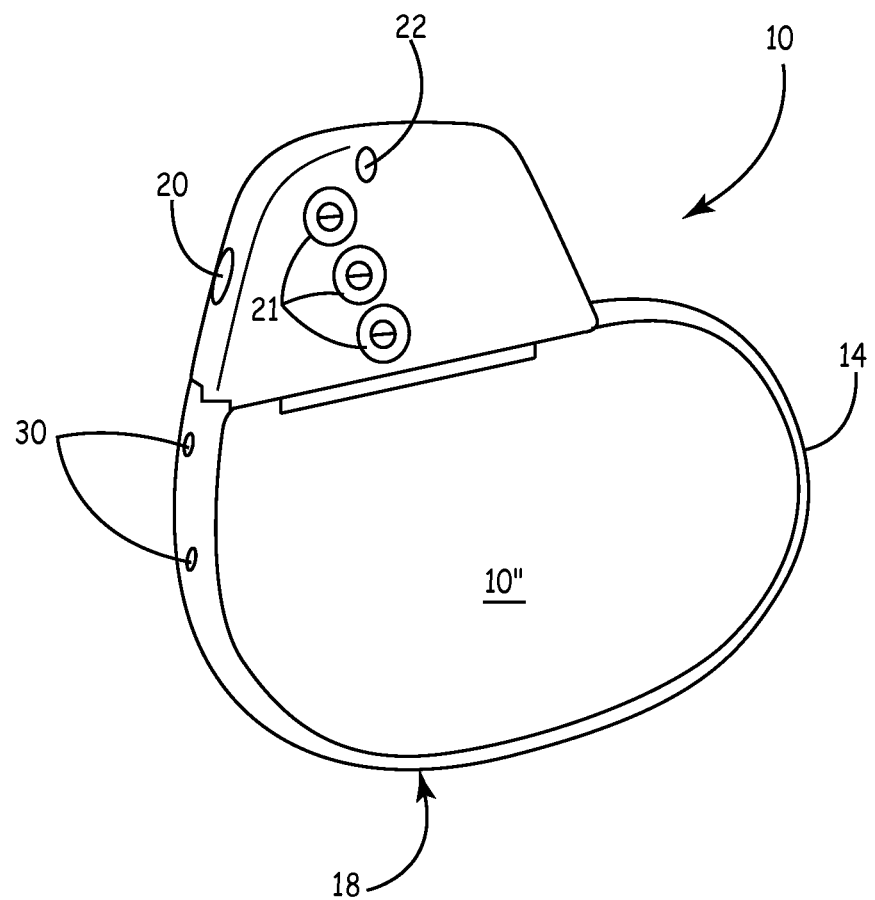
FIG. 3 is a perspective view of an opposing major side of the IMD depicted in FIGS. 1 and 2.
Figure 6:
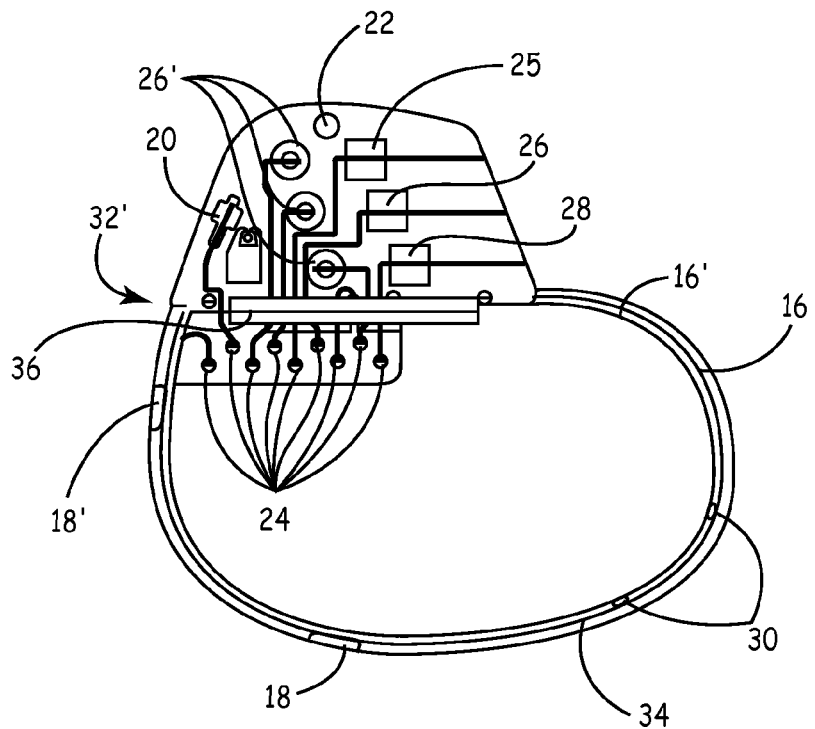
FIG. 6 is a view of a second side of the transparent shroud assembly coupled to a header according to the invention that clearly illustrates that the conductors and components of the assembly are readily visible from both sides.

FIG. 3 is a perspective view of an opposing major side 10" of the IMD 10 depicted in FIGS. 1 and 2 and three self-healing grommets 21 substantially hermetically coupled to openings of a like number of threaded bores (shown in FIG. 6 and denoted by reference numeral 26'). As is known, the threaded bores are configured to receive a threaded shank and the grommets 21 are fabricated to temporarily admit a mechanical tool (not shown). The tool is used to connect and allow a physician or clinician to manually tighten the conductors 25,26,28, for example, with compression and/or radially around conductive rings disposed on proximal portions of medical electrical leads (not shown). In addition, two of the plurality of ports 30 are also depicted in FIG. 3.

Figure 4:
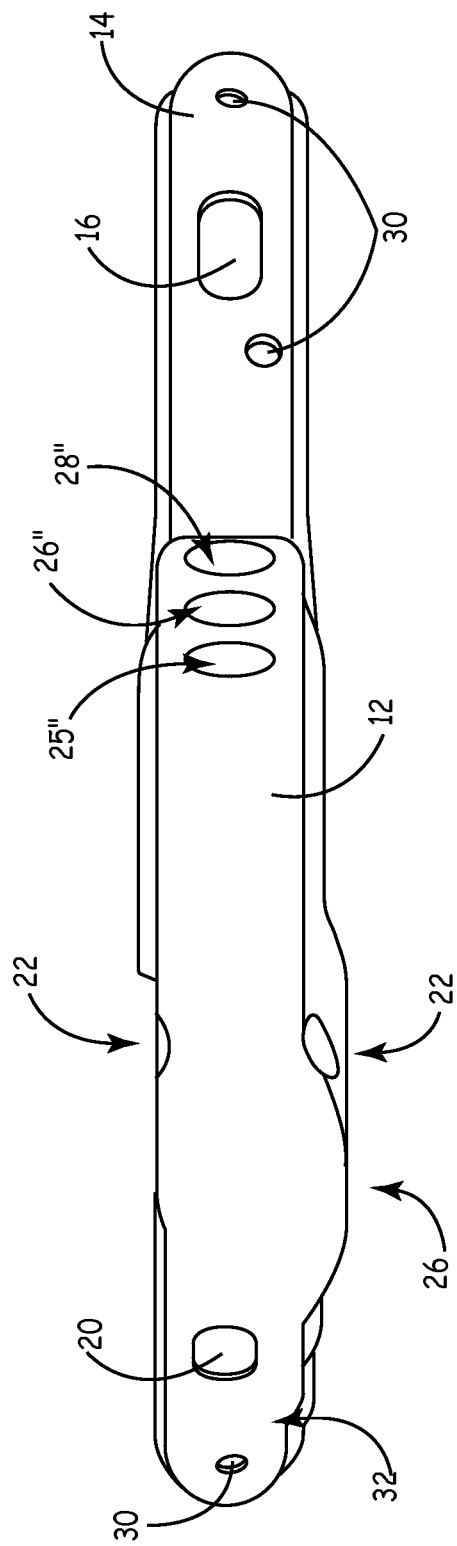
FIG. 4 is a plan view of the IMD previously depicted that illustrates the relationship between two of the electrodes coupled to the shroud assembly as well as depicting the header, or connector, of the IMD.

FIG. 4 is a plan view of the IMD 10 previously depicted that illustrates the relationship between two of the electrodes 16,20 coupled to the shroud assembly 14 as well as depicting the header 12, or connector, of the IMD 10. Opposing openings of the aperture 22 formed in the header 12 are also depicted in FIG. 4 as are the three openings 25",26",28" of the bores or ports formed in the header 12 that are configured to admit the proximal end of medical electrical leads (not shown). Three of the adhesive-admitting ports 30 are shown distributed at various locations through the surfaces of the shroud 14.

Three elongated conductors individually couple to a respective electrode 14,16,18. These elongated conductors can be continuous or discrete segments of conductive material. In the event that they comprise discrete segments, they need to be coupled together such as with convention means like laser bonding, welding, soldering and the like. For example, the elongated conductor coupling to electrode 16 can traverse either direction around the periphery of the IMD 10 disposed within or mechanically coupled to an inner portion of the shroud 14. If it traverses past the seam 32 it might need to be isolated from the elongated conductor coupled to electrode 18 (assuming that conductor also traversed seam 32). If the conductor coupling electrode 16 is routed directly toward the header 12 (and the header/shroud is not a unitary structure) then a bond between segments of the elongated conductor could be necessary at the junction of the shroud 14 and the header 12.

Figure 5:
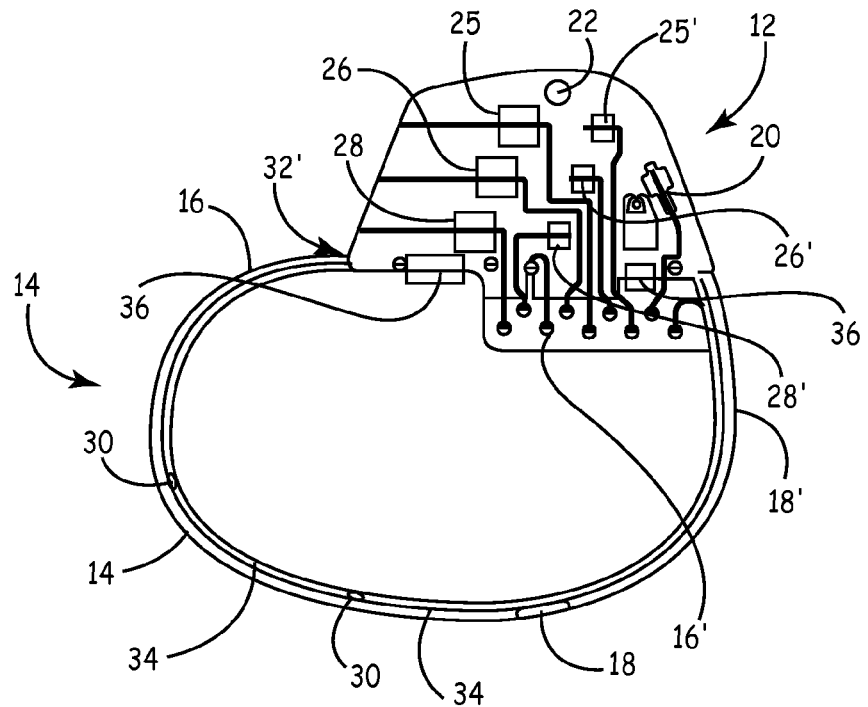
FIG. 5 is a view of a first side of a transparent shroud assembly coupled to a header according to the invention that clearly illustrates that the conductors and components of the assembly are readily visible.

FIG. 5 is a view of a first side of a transparent shroud assembly 14 coupled to a header 12 according to the invention that clearly illustrates that the conductors and components of the assembly are readily visible. FIG. 6 is a view of a second side of the transparent shroud assembly coupled to a header according to the invention that clearly illustrates that the conductors and components of the assembly are readily visible from both sides.

Since FIG. 5 and FIG. 6 essentially depict common components of the inventive assembly of the invention they shall be described together. The exemplary shroud assembly 14 of FIGS. 5 and 6 is depicted with an IMD 10 for clarity. The electrical conductors 25,26,28 disposed in the header, or connector, portion 12 of the IMD 10 are configured to couple to end portions of medical electrical leads as well as couple to operative circuitry within the IMD housing (not shown). The shroud assembly 14 mechanically couples to the header portion 12 at each end of the shroud assembly 14 both mechanically and electrically via medical adhesive (disposed at overlapping joint 32') and an elongate conductor 16' (passing through joint 32'). The three discrete electrodes 16,18,20 and their corresponding elongated conductors 16',18', 20' are coupled together. While not depicted in FIGS. 5 and 6 the conductors 16',18',20' have at least a partially serpentine configuration and conductors 16',18' are furthermore mechanically coupled to the shroud with a series of elongated stand-off bosses 34. In addition, and as previously mentioned, during attachment to an IMD adhesive is disposed intermediate the shroud 14 and the IMD with excess being evacuated from ports 30 (and/or if needed injected into one of more ports 30) to eliminate any air bubbles. Of course, one feature of the invention relates to the ability to fully inspect the finished article visually (including the quality of the electrical connections and the quality of the bond between the shroud 14 and an IMD. Also, the electrodes 16,18 can be at least one of mechanically embedded partially into the material of the shroud 14 and configured to receive medical adhesive to retain the electrodes in position (e.g., using perforated wing-like peripheral portions of the electrodes disposed at the ends, sides, and/or other parts of the periphery of an electrode). Aperture 22 also can be seen in FIGS. 5 and 6 formed in a peripheral portion of the header 12. Also depicted is how the elongated conductor 14' couples to electrode 14, elongated conductor 16' couples to electrode 16, and conductor segment 20' couples to electrode 20. Furthermore, three of the conductors (denoted collectively with reference numeral 24) couple to three cuff-type conductors 25,26,28 adapted to receive proximal portions of medical electrical leads while another three of the conductors couple to conductive pads 25',26',28' which are aligned with, but spaced from the conductors 25,26,28 along a trio of bores (denoted as 25",26",28" in FIG. 4 herein) formed in header 12. The joint 32 between header 12 and shroud 14 can comprise a variety of mechanisms, including an interlocking, partially spring-biased socket-type connection which, in combination with medical adhesive, provides a reliable mechanical coupling.

Another feature of the invention relates to including radio-opaque markers and/or identifiers within and/or on the shroud 14 so that a physician or clinician can readily determine that an IMD is outfitted with an assembly according to this invention. A marker according to this aspect of the invention can include a metallic insert and/or coating having a unique shape, location and/or configuration (e.g., an "M" or the corporate logo for an IMD manufactured by Medtronic, Inc.).

Depicted in FIGS. 5 and 6 is an elongated structural support member 36 which provides a reliable connection to a metallic housing of an IMD (not shown) via traditional processes (e.g., laser welding). The member 36 has a three substantially orthogonal sides (all denoted as 36 in FIGS. 5 and 6) thus providing three discrete bonding areas between the header 12 and an IMD. Of course, the member 36 could be perforated and/or coated with an insulative material, but in the embodiment depicted one side is cut out or not present so that the plurality of conductors 24 can pass from the header 12 and shroud 14 to the feedthrough array of the IMD.

Electrodes 16,18,20 and/or the (corresponding elongated conductors) can be fabricated out of any appropriate material, including without limitation tantalum, tantalum alloy, titanium, titanium alloy, platinum, platinum alloy, or any of the tantalum, titanium or platinum group of metals whose surface may be treated by sputtering, platinization, ion milling, sintering, etching, or a combination of these processes to create a large specific surface area. Also as noted herein, an electrode can be stamped, drawn, laser cut or machined using electronic discharge apparatus. Some of the foregoing might require de-burring of the periphery of the electrode or alternately any sharp edges due to a burr can be coupled facing toward the corresponding recess in the shroud member thereby minimizing likelihood of any patient discomfort post-implant while further reducing complexity in the fabrication of assemblies according to the invention. The electrodes can be coated or covered with platinum, a platinum-iridium alloy (e.g., 90:10), platinum black, titanium nitride or the like.

Figure 7:
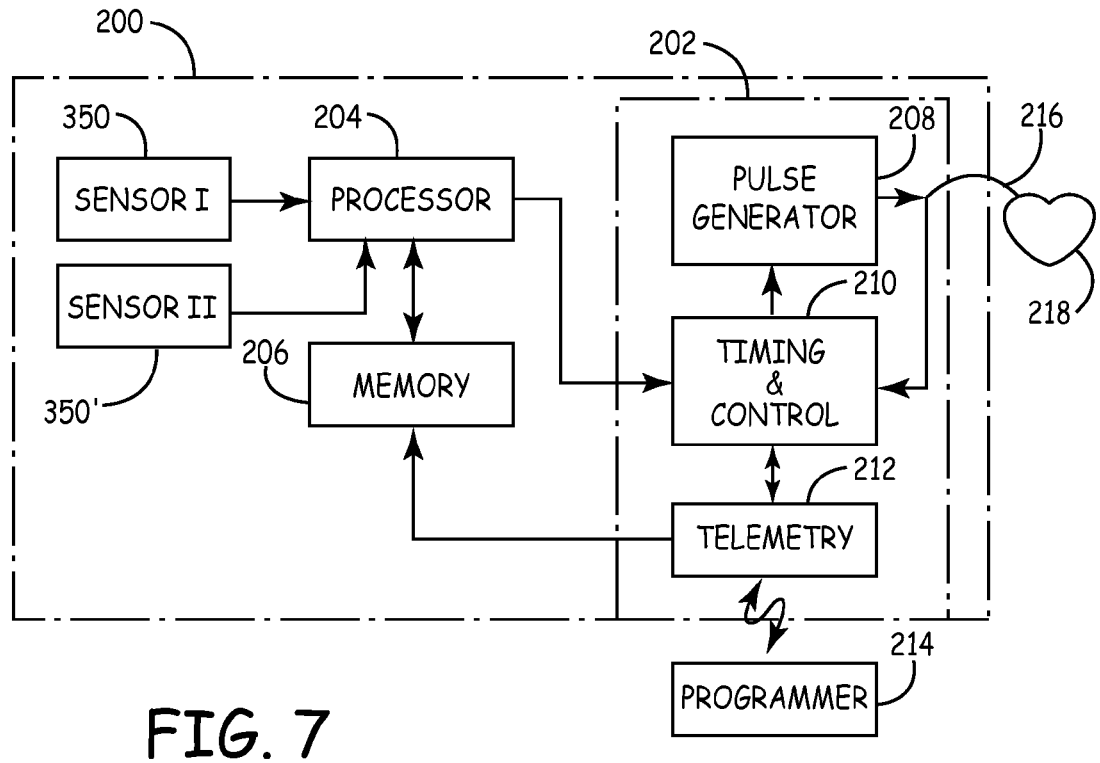
FIG. 7 is a schematic block diagram of a rate-responsive IPG including an accelerometer-based, multi-axis physical activity sensor according to the present invention.

Referring now to FIG. 7, a block diagram illustrating the operation of an IPG 200 that uses a signal representative of physical activity provided by a first (traditional) patient-activity sensor 350 is described. The first sensor 350 can be fabricated of diverse materials and employ known circuitry and the like. The IPG 200 includes an IPG circuit 202 (which may be conventional), the patent-activity sensor 350 (denoted "SENSOR I"), a second patient-activity sensor 350' (denoted "sensor II"), a processor 204 coupled to the first sensor 350 and the second sensor 350', and a memory circuit 206 coupled to processor 204. Although the first sensor 350 is depicted to be within the housing (denoted by dashed lines) the IPG 200 the first sensor 350 may alternatively be externally located, and indeed, may even be remotely located, such as at a suitable location on or within a pacing lead (denoted schematically as line segment 216).

The IPG circuit 202 includes a pulse generator circuit 208, a timing and control circuit 210 coupled to the pulse generator circuit 208 and to the processor 204, and a telemetry circuit 212. The telemetry circuit 212 telemetrically communicates with an external programmer 214, and is coupled within the IPG 200 to the memory circuit 206 and the timing and control circuit 210.

Coupled to the pulse generator circuit 208 is at least one pacing lead 216, which may be conventional. The pacing lead 216 is used to deliver pacing pulses provided by the pulse generator circuit 208 to a patient's heart 218. In addition, the pacing lead 216 senses intrinsic activity of the heart 218, and presents a signal indicative thereof to the timing and control circuit 210. Thus, the IPG 200 is capable of operating in a "demand mode," in which delivery of a pacing pulse is inhibited by the timing and control circuit 210 when an intrinsic cardiac contraction is sensed during the escape interval following a preceding contraction.

Although the following description assumes that the IPG 200 is operating in a demand mode, it should be understood that a simpler implementation is possible, in which the IPG 200 does not inhibit delivery of pacing pulses when intrinsic contractions are sensed, but still changes the patient's heart rate in response to the output of the first sensor 350 and/or the second sensor 350'. Also, a demand mode may be a telemetrically programmable feature, allowing the IPG 200 to be switched into and out of demand mode when desired by a physician using programmer 214 and/or a magnet coupled to a so-called "reed switch" or other switching mechanism.

In operation, the first sensor 350 responds to bodily accelerations associated with physical activity in directions along a plurality of axes. A sensor signal is generated by the first sensor 350, which is indicative of the level to which the patient is engaged in physical activity. For the purposes of this discussion, a processing circuit (not shown) can be incorporated within the sensor 350, although other arrangements are possible. The sensor signal from first sensor 350 is provided to the processor 204, which further processes the signal from the first sensor 350 using techniques which may be conventional (e.g., averaging, half-wave rectification, full-wave rectification) to determine a current level of physical activity. The processor 204 in turn provides a rate control signal to the timing and control circuit 210, which determines the heart rate to be maintained by the IPG 200. In one embodiment, the rate control signal provided by the processor 204 adjusts the escape interval used by the timing and control circuit 210, which has the effect of increasing or decreasing the maintained heart rate. It should again be noted that the IPG 200 can also be telemetrically programmed by the programmer 214 to operate in a constant rate mode if desired by the physician.

Figure 8:
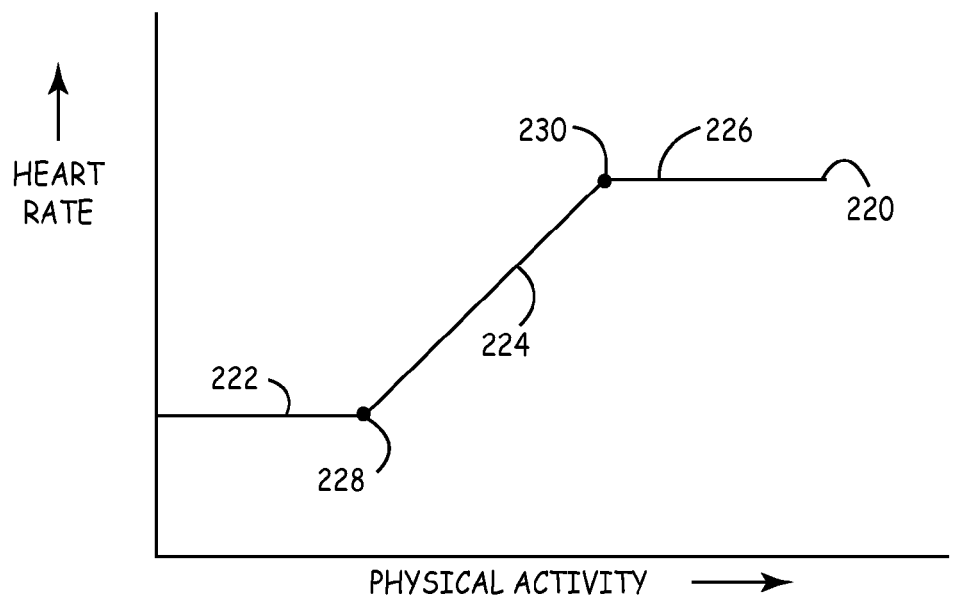
FIG. 8 depicts a representative transfer curve used by a rate-responsive IPG according to the present invention.

The manner by which the IPG 200 adjusts the maintained heart rate in accordance with a signal provided by the first activity sensor 350 of the present invention may be understood by reference to a transfer curve 220 shown in FIG. 8. The transfer curve 220 correlates physical activity (as measured by the first sensor 350 shown in FIG. 7) along the horizontal axis with a desired heart rate along the vertical axis. The transfer curve 220 has three segments—a minimum rate segment 222, a slope segment 224, and a maximum rate segment 226, each of which may be telemetrically varied to meet the needs of a particular patient. For example, a physician (not shown) may set the minimum rate segment 222 at 60 beats per minute, and may set a first activity threshold 228 at a relatively low level of physical activity that is required before the IPG 200 (FIG. 7) abandons the heart rate defined by the minimum rate segment 222 in favor of a heart rate determined by the slope segment 224. The physician may set the maximum rate segment 226 at, for example, 120 beats per minute, and may set a second activity threshold 230 at a relatively high level of physical activity that is required before the IPG 200 (FIG. 7) discontinues using the slope segment 224 in favor of the heart rate corresponding to the maximum rate segment 226. In addition, the slope segment 224 may be telemetrically adjustable, so that changes to the maintained heart rate may be more gradual or more aggressive, depending upon the needs of a particular patient.

Information defining the transfer curve 220 is stored in the memory 206 (FIG. 7) of the IPG 200 (FIG. 7) in a conventional manner. For example, the transfer curve 220 may be stored as a collection of discrete data points in a look-up table (not shown). Alternatively, the minimum rate segment 222 and the maximum rate segment 226 may be stored discretely, and the slope segment 224 may be stored as a mathematical algorithm which is used by the processor 204 (FIG. 7) to compute the appropriate heart rate to be maintained when the determined level of physical activity as measured by the sensor 350 (FIG. 7) falls between the first activity threshold 228 and the second activity threshold 230.

Figure 9:
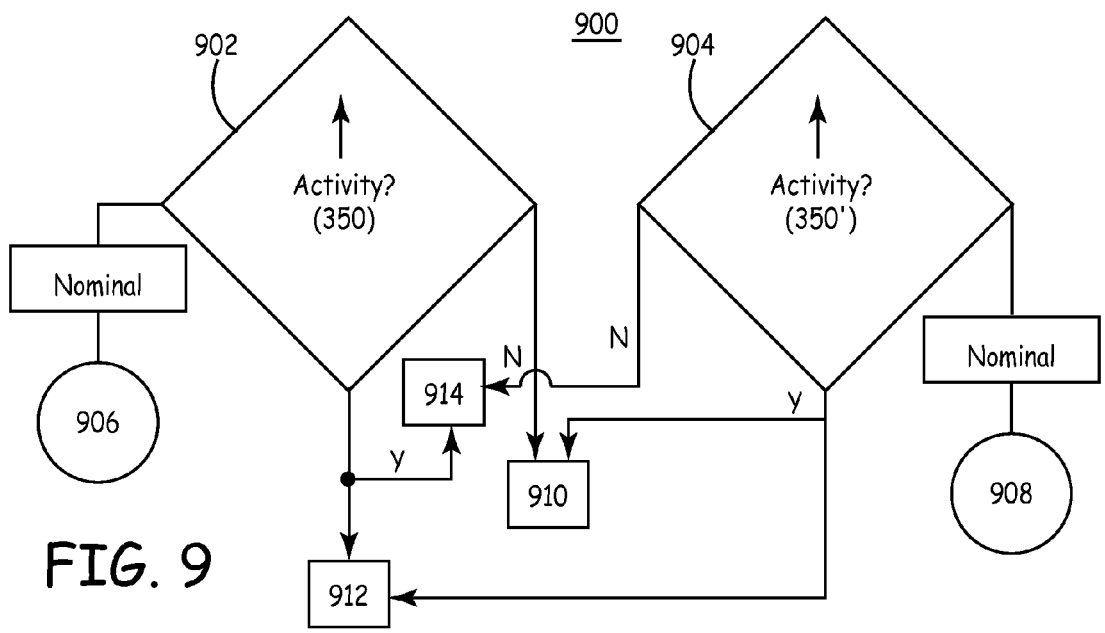
FIG. 9 is a simplified flow chart illustrating how the dual sensor rate responsive IPG of the invention can be programmed to respond to changing (i.e., increasing) detected activity levels of a subject.

FIG. 9 is a simplified flow chart 900 illustrating how the dual sensor rate responsive IPG of the invention can be programmed to respond to changing (i.e., increasing) detected activity levels of a subject. As illustrated in FIG. 9, a signal from sensor 350 (at 902) can indicate a nominal (e.g., slowly changing or unchanging), indication of an essentially global patient activity level, an essentially global increasing patient activity level, or an essentially global decreasing patient activity level. Although increasing activity is queried in FIG. 9 the logical not ("N") can be used to indicate a decreasing detected patient activity level.

In a similar manner, at 904 the electrode-based patient activity sensor 350' provides a signal that essentially indicates the level and/or changes in the level of relatively localized patient activity (e.g., primarily upper body). In one embodiment of the invention the signals from sensor 350' are collected for a period of time and can be averaged, time weighted, or otherwise mathematically manipulated so that any spurious signals or transient signals do not rapidly affect the rate response of the IPG. Similarly, time-rate-of-change (mathematical derivative) values such as minimum, maximum, positive and negative values can be used as can threshold crossing events, fiducial points, and other techniques known and/or used in the art.

Sampling of the signal from sensor 350' can be continuous although myopotential "noise" can be more readily detected during repolarization of the ventricles (i.e., during the S-T segment) or otherwise during a relatively quiescent period of time. The signal from sensor 305' can also be suitably filtered to remove frequencies that are unlikely to correlate to patient exertion. The signal from sensor 305' can also be affected by the location of the implanted IMD such that a pectorally-implanted IMD might require different filtering than an IMD The signals from the sensors 350,350' can both indicate a nominal or essentially unchanging low level of detected patient activity (at 906,908). In this scenario the pacing rate (bpm) should be at a relatively lower programmed level or, in the event that a presently high rate of pacing therapy is being delivered, gradually lowered.

Figure 10:
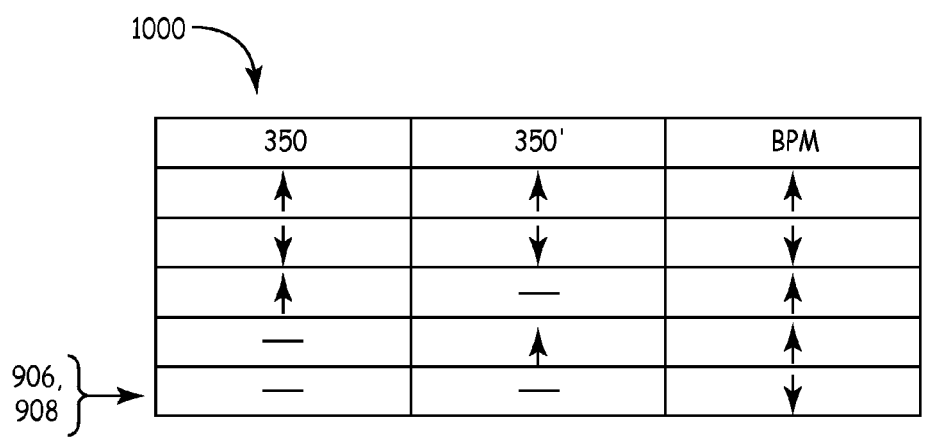
FIG. 10 illustrates in a different manner how the rate responsive pacing rate (expressed in beats per minute, or bpm) can be affected by various combinations of signals sensed from a pair of sensors according to the invention.

FIG. 10 illustrates in a different manner how the rate responsive pacing rate (expressed in beats per minute, or bpm) can be affected by various combinations of signals sensed from a pair of sensors according to the invention. In FIG. 10 a dash ("-") denotes a nominal or relatively low or slowly changing detected level of patient activity. An upward-oriented arrow denotes a rising or high level of detected patient activity and a downward-oriented arrow denotes a declining or low level of detected patient activity.

It should be appreciated that the electrode-based sensor 350' can be used only in certain situations. For instance, as a back-up to confirm a null, nominal or low level of detected patient activity from sensor 350. In addition or in lieu of the foregoing signals from the sensor 350' could be sampled primarily when the programmed or rate-responsive pacing rate declines below a certain level. This helps ensure that a patient rarely enters a situation wherein hemodynamic performance (e.g., perfusion of oxygen, etc.) is compromised.

Accordingly, a number of embodiments and aspects of the invention have been described and depicted although the inventors consider the foregoing as illustrative and not limiting as to the full reach of the invention. That is, the inventors hereby claim all the expressly disclosed and described aspects of the invention as well as those slight variations and insubstantial changes as will occur to those of skill in the art to which the invention is directed. The following claims define the core of the invention and the inventors consider said claims and all equivalents of said claims and limitations thereof to reside squarely within their invention.

The invention claimed is:

1. A method of controlling a rate responsive cardiac pacing scheme, comprising:
   receiving a non-myopotentially-based patient activity sensor signal from a sensor coupled to an implantable medical device (IMD);
   receiving a myopotential-based patient activity sensor signal from at least a pair of surface electrodes mechanically coupled to a portion of the IMD; and
   logically combining the non-myopotentially-based patient activity sensor signal and the myopotentially-based patient activity signal to control a rate responsive cardiac pacing scheme of the IMD; and delivering cardiac pacing to the patient according to the rate responsive pacing scheme;
   further comprising filtering the non-myopotentially-based patient activity sensor signal and the myopotentially-based patient activity signal prior to logically combining the non-myopotentially-based patient activity sensor signal and the myopotentially-based patient activity signal.

2. A subcutaneously implantable device, comprising:
   a subcutaneously implantable device housing;
   a patient activity sensor disposed within the device housing providing a patient activity output signal;
   a pair of spaced apart subcutaneous electrodes mounted to the device housing;
   circuit means for receiving, processing, and filtering the patient activity output signal and for receiving, processing, and filtering myopotential signals from the electrodes and for providing both a non-myopotential-based patient activity signal and an a myopotential-based patient activity signal therefrom and for logically combining the myopotential-based patient activity signal and the non-myopotential-based patient activity to control a rate responsive cardiac pulse stimulator.

3. A device according to claim 2, wherein the patient activity sensor disposed within the device housing comprises a piezoelectrically-based motion sensor.

4. A device according to claim 2, wherein said patient activity sensor disposed within the device housing comprises one of a single axis accelerometer and a multi-axis accelerometer.

5. A device according to claim 2, wherein the IMD comprises one of an implantable cardiac pacemaker and an implantable cardioverter-defibrillator.

6. A subcutaneously implantable device, comprising:
   a subcutaneously implantable device housing;
   a patient activity sensor disposed within the device housing providing a patient activity output signal;
   a pair of spaced apart subcutaneous electrodes mounted to the device housing;
   circuit means for receiving, processing, and filtering the patient activity output signal and for receiving, processing, and filtering myopotential signals from the electrodes and for providing both a non-myopotential-based patient activity signal and an a myopotential-based patient activity signal therefrom and for logically combining the myopotential-based patient activity signal and the non-myopotential-based patient activity to control a rate responsive cardiac pulse stimulator; and
   further comprising filters which filter the non-myopotentially-based signal and the myopotentially-based signal prior to logically combining the non-myopotentially-based signal and the myopotentially-based signal.

7. A subcutaneously implantable device, comprising:
   a subcutaneously implantable device housing;
   a patient activity sensor disposed within the device housing providing a patient activity output signal;
   a pair of spaced apart subcutaneous electrodes mounted to the device housing;
   circuit means for receiving, processing, and filtering the patient activity output signal and for receiving, processing, and filtering myopotential signals from the electrodes and for providing both a non-myopotential-based patient activity signal and an a myopotential-based patient activity signal therefrom and for logically combining the myopotential-based patient activity signal and the non-myopotential-based patient activity to control a rate responsive cardiac pulse stimulator; and
   wherein the circuit means for logically combining the non-myopotential-based and the myopotentially-based patient activity signals employs the myopotentially-based patient activity signals to confirm a low level of detected patient activity indicated by the non-myopotentially-based patient activity signal.

8. A subcutaneously implantable device, comprising:
   a subcutaneously implantable device housing;
   a patient activity sensor disposed within the device housing providing a patient activity output signal;

a pair of spaced apart subcutaneous electrodes mounted to the device housing;

circuit means for receiving, processing, and filtering the patient activity output signal and for receiving, processing, and filtering myopotential signals from the electrodes and for providing both a non-myopotential-based patient activity signal and an a myopotential-based patient activity signal therefrom and for logically combining the myopotential-based patient activity signal and the non-myopotential-based patient activity to control a rate responsive cardiac pulse stimulator; and wherein the circuit means for logically combining the non-myopotential-based and the myopotentially-based patient activity signals employs the myopotentially-based patient activity signals responsive to a cardiac pulse rate falling below a defined level.

9. A method of controlling a rate responsive cardiac pacing scheme, comprising:

receiving a non-myopotentially-based patient activity signal from a sensor coupled to an implantable medical device (IMD) implanted within a patient;

deriving a myopotential-based patient activity signal from at least a pair of surface electrodes mechanically coupled to a portion of the IMD; and logically combining the non-myopotentially-based patient activity signal and the myopotentially-based patient activity signal to control a rate responsive cardiac pacing scheme of the IMD; and delivering cardiac pacing to the patient according to the rate responsive pacing scheme;

wherein logically combining the non-myopotential-based and the myopotentially-based patient activity signals comprises employing the myopotentially-based patient activity signals to confirm a low level of detected patient activity indicated by the non-myopotentially-based patient activity signal.

10. A method of controlling a rate responsive cardiac pacing scheme, comprising:

receiving a non-myopotentially-based patient activity signal from a sensor coupled to an implantable medical device (IMD) implanted within a patient;

deriving a myopotential-based patient activity signal from at least a pair of surface electrodes mechanically coupled to a portion of the IMD; and logically combining the non-myopotentially-based patient activity signal and the myopotentially-based patient activity signal to control a rate responsive cardiac pacing scheme of the IMD; and delivering cardiac pacing to the patient according to the rate responsive pacing scheme;

wherein logically combining the non-myopotential-based and the myopotentially-based patient activity signals comprises employing the myopotentially-based patient activity signals employs the myopotentially-based patient activity signals responsive to a cardiac pacing rate falling below a defined level.

\* \* \* \* \*